(12) United States Patent
Yang et al.

(10) Patent No.: US 6,989,277 B2
(45) Date of Patent: Jan. 24, 2006

(54) METHOD FOR IMMUNOASSAYS BASED ON INFRARED REFLECTION ABSORPTION SPECTROSCOPY

(75) Inventors: Jyisy Yang, Taichung (TW); Yu-Ching Liu, Taichung (TW); Shyhliang A. Lou, Hsinchu (TW)

(73) Assignee: Industrial Technology Research Institute, Hsin Chu Hsien (TW)

( * ) Notice: Subject to any disclaimer, the term of this patent is extended or adjusted under 35 U.S.C. 154(b) by 53 days.

(21) Appl. No.: 10/448,400

(22) Filed: May 30, 2003

(65) Prior Publication Data

US 2004/0115729 A1 Jun. 17, 2004

(30) Foreign Application Priority Data

Dec. 17, 2002 (TW) ............................ 91136387 A

(51) Int. Cl.
*G01N 33/543* (2006.01)

(52) U.S. Cl. .................... 436/518; 436/501; 435/4; 435/7.1; 435/7.4; 435/7.92; 435/7.93; 435/7.94; 435/7.95; 422/82.05; 422/55; 422/57; 422/68.01; 422/82.01; 250/339.12; 250/339.06; 250/458.1; 250/244

(58) Field of Classification Search ................ 436/518, 436/501; 435/4, 7.1, 7.4, 7.92–7.95; 422/82.05, 422/55, 57, 68.01; 250/339.12, 339.06, 458.1, 250/244

See application file for complete search history.

(56) References Cited

U.S. PATENT DOCUMENTS

| 4,975,581 | A | * | 12/1990 | Robinson et al. ....... 250/339.09 |
| 5,620,856 | A | * | 4/1997 | Carlson et al. .............. 435/7.1 |
| 5,716,854 | A | * | 2/1998 | Lofas et al. ................ 436/518 |
| 5,977,545 | A | * | 11/1999 | Haar et al. ............. 250/339.12 |
| 6,284,197 | B1 | * | 9/2001 | Abbott et al. ............ 422/82.05 |
| 6,313,914 | B1 | * | 11/2001 | Roe ........................... 356/301 |
| 6,699,724 | B1 | * | 3/2004 | West et al. ................. 436/525 |

* cited by examiner

*Primary Examiner*—Pensee T Do
(74) *Attorney, Agent, or Firm*—Bacon & Thomas, PLLC

(57) ABSTRACT

This invention relates to a method for immunoassays based on infrared reflection absorption spectroscopy that utilizes proteins such as antigen and antibody that have specific absorptions in infrared absorption spectrum under 1550 $cm^{-1}$. A chip is made from infrared reflective substrates such as a gold or silver plate, whereon the antibodies or antigens are immobilized by the specific bonding action between metal surfaces of the chip and proteins, and the protein signals are then detected by infrared reflection-absorption and infrared microscopy. Since infrared radiation is capable of interacting with any organic molecules, there is no need to label the samples with fluorescent reagents or nucleic irradiation reagent. This invention thus provides a label-free process that can avoid the inconvenience of labeling common biochemical material for detection in the prior art, thus achieving the purpose of higher speed of detection.

9 Claims, 3 Drawing Sheets

METHOD FOR IMMUNOASSAYS BASED ON INFRARED REFLECTION ABSORPTION SPECTROSCOPY

BACKGROUND OF THE INVENTION

1. Field of the Invention

The present invention is a method for immunoassays by using infrared reflection absorption spectroscopy. Essentially, the invention immobilizes protein molecules such as antigen or antibody on an infrared reflective substrate and detects the signals of the proteins by using the infrared reflection absorption spectroscopy. The present invention can be applied on the biosensor detection field.

2. Description of the Related Arts

Among the many types of biological assay techniques, immunoassay has been gaining favorable recognitions in recent years, because one positive attribute is that it uses proteins that each reacts quite exceptionally; hence, immunoassays have a higher level of sensitivity than other assay techniques. Essentially, immunoassays rely on general principles in immune reactions by taking an antibody and an antigen that was recognized mutually and combining them into a complex. This antibody-antigen complex is then used to determine the existence of antibody and antigen in a given medium.

When determining a method of detection that uses an antigen-antibody complex, scientists often rely on electrical and electrochemical, mass-sensitive, magnetic or optical, as well as other detecting means. Basically, electrical or electrochemical detecting means measure changes in electrode surface mass concentration caused by electron transfer reactions. Mass-sensitive detecting means interpret signals released by a change in mass. Magnetic detecting means use paramagnetic tracers to sense strength of magnetic field for determination of the concentration of the reactant. Optical detecting means begin with tagging a probe (such as biological fluorescent matter, chemical light emission material or dye) on the matter to be measured. When the matter and the probe have undergone biological reactions, the probe generates optical signals to be measured. Current optical detectors are primarily based on principles of light emission, surface plasmon resonance and evanescent wave absorption.

Principles of light emission, such as fluorescence or luminescence, are very well used because they can generate information that can be detected very quickly and directly. However, the immunoassays based on fluorescence generally require that a sandwich be formed by combining the antibody-antigen with a labeled antibody; thus this is not a single-step process. Furthermore, the fluorescence interference is often encountered in the UV-visible region due to naturally occurring or other contaminating fluorophores; this has led to major efforts to develop near-IR fluorophores for labeling the antibodies, since naturally occurring fluorescence is mostly confined to the UV-visible regions.

In the detection of surface plasmon resonance, the antibody molecule is immobilized on the metal surface such as gold or silver, which was previously deposited on the base of the optically transparent prism. Polarized light is incident with the appropriate resonance angle into the prism as to cause a resonance of light waves inside of the metal surface. The resonance angle would change when the media on the metal surface has a different refractive index. Such change can be used for assaying biomolecules. Although surface plasmon resonance is a very sensitive technique that allows for immediate detection of matters, it suffers from the fact non-specific absorption can occur on the immobilized surfaces, e.g., proteins can cling to the surface and cause a change in wavelength or angle of maximum resonance, and this would be falsely interpreted as the antigen.

Evanescent wave measuring means has been used in immunoassays in recent years. Such method of measurement is preferred for being direct and quick. Evanescent wave is generated on the interface of two light media. When the interfacing angle exceeds a critical angle, light wave will be total internal reflected from a heavy meson. Evanescent wave then is the electromagnetic wave that pierces through the heavy meson. However, the problem with evanescent wave measuring means is that there are very limited amount of parts for such device and that it can only measure one matter at a time, making measuring a large amount of matters very difficult.

There are many inconveniences in contemporary light spectroscopy, such as the difficulty in labeling light probes in fluorescence or luminescence techniques, or signal interference in the background. Thus, many have tried to develop new optical spectroscopy techniques. Among the new techniques being developed, infrared light has received a lot of attention as a new technique in light spectroscopy.

Infrared spectroscopy has contributed to protein structure analysis in the past and it is useful for the characterization of protein secondary structure and the identification of protein components. Since most biomolecules have specific IR spectra, it is possible to isolate structural effects of a protein interacting with substrates. This principle can be applied to bioassay in a biosensor. Infrared light allows experimenters to quickly obtain full light spectrum, and to easily prepare samples. Furthermore, infrared light can eliminate problems associated with the need for light probes in fluorescent light spectroscopy. Hence the present invention utilizes infrared spectroscopy to solve problems stated above.

SUMMARY OF THE INVENTION

The present invention eliminates problems with the requirement of probe labeling in traditional measuring techniques that uses biosensors. Since most biomolecules have specific IR spectra, it is possible to detect interaction effects of a protein-substrate complex such as antibody-antigen by changes in spectra between presence and absence of binding. Hence the present invention utilizes infrared spectroscopy on biosensors for measurement.

Because acid groups in the proteins have special ability to interact with a metal such as gold or silver and to form stable bond with the metal, proteins can be immobilized on a metal; thus this minimizes the immobilization step for biosensor preparation. Once fixed on the metal, they are subject to infrared spectroscopy detection device that obtains their respective light absorption signals.

This invention uses an infrared immunoassay method that comprises the following steps: providing an infrared reflective substrate; immobilizing the known molecule on the substrate; blocking the non-specific binding site of the molecule; hybridizing the analyte of interest with the known molecule that are immobilized on the substrate; and detecting the IR reflection absorption signal by using the IR spectroscopy.

The above-mentioned substrate can be either metallic template or a substrate covered metallic layer. Possible choices of metal include gold, silver, copper, aluminum, germanium or stainless steel. The more preferable choices of metal are gold and silver.

The above-mentioned molecule is intended for use in a molecular recognition-based assay for the analysis of a sample suspected of containing an analyte of interest. The above-mentioned molecule can be protein, antibody, antigen or receptor and the like. The more preferable choices are antibody and antigen. The above-mentioned analyte of interest can be DNA, ligand, antibody, and antigen. The molecule can interact with the analyte of interest in the test sample solution to form a specific binding complex through their binding affinity, e.g. protein-protein (such as antibody-antigen), protein-DNA, and protein-ligand (such as receptor-hormone).

The above-mentioned blocking procedure includes dissolving a blocking agent with a liquid buffer and treating the surface of the substrate with said blocking agent blocks the non-specific binding site of the molecule and which does not interfere with the interaction between the known molecule and the analyte of interest. Blocking refers to physically interfering with the binding interaction between the binding site and the blocking agent by, for example, covering or masking part of or all of the binding site, interfering with access of the protein to the binding site (sterically or by charge), or otherwise interfering with binding. Blocking agents generally include any molecular species such as BSA, or dry milk and etc. However, the material described above is protein, and it is not possible to determine whether the signal detected is that of the probe-target molecule (e.g. antibody-antigen) or is interference coming from the blocking agent. Hence, the present application chooses low infrared light absorption molecule as a blocking agent, because such molecule can form hydrogen bonds with the $OH^-$ or $NH_2$ groups on the protein and allows blocking of non-specific sites of the proteins. Said molecule can be selected from the following: glucose, glycerol, polyallylamine, and polyvinyl alcohol. The more preferable selections are polyvinyl alcohol and polyallylamine.

Another aspect in the present invention is the method for detecting biosensors by using infrared reflection absorption spectroscopy, comprising the following steps: providing an IR reflective substrate; immobilizing the known molecule on the substrate as a probe; blocking the sites of non-specific absorption; hybridizing the target molecule with the probe which immobilized on the substrate; and detecting the IR reflection absorption signal by using the IR spectroscopy.

The above-mentioned infrared reflection absorption spectroscopy is best used to detect antibody-antigen complexes. Comparative to traditional detected methods, a main positive attribute in the invented spectroscopy is that there is no need to label the molecule with lighting or emission matters to be tested and still can provide adequate detection.

DETAILED DESCRIPTION

The object of the present invention is to provide biosensor based on IR spectrum immunoassay. The three dominant bands in any protein's absorbance spectrum are the amide I (1670 $cms^{-1}$), amide II (1550 $cm^{-1}$), and amide III (1230 $cm^{-1}$). These peaks are sensitive to hydrogen-bonding interaction, and therefore they are sensitive to differences in proteins. Therefore, each protein has specific IR spectra that allows for spectroscopic detection. Among the three amides, amide I has the greatest absorption peak that overlaps with water absorption, making it prone to interference. For that reason, amide II is the more appropriate choice for determining a protein.

Figure 1:
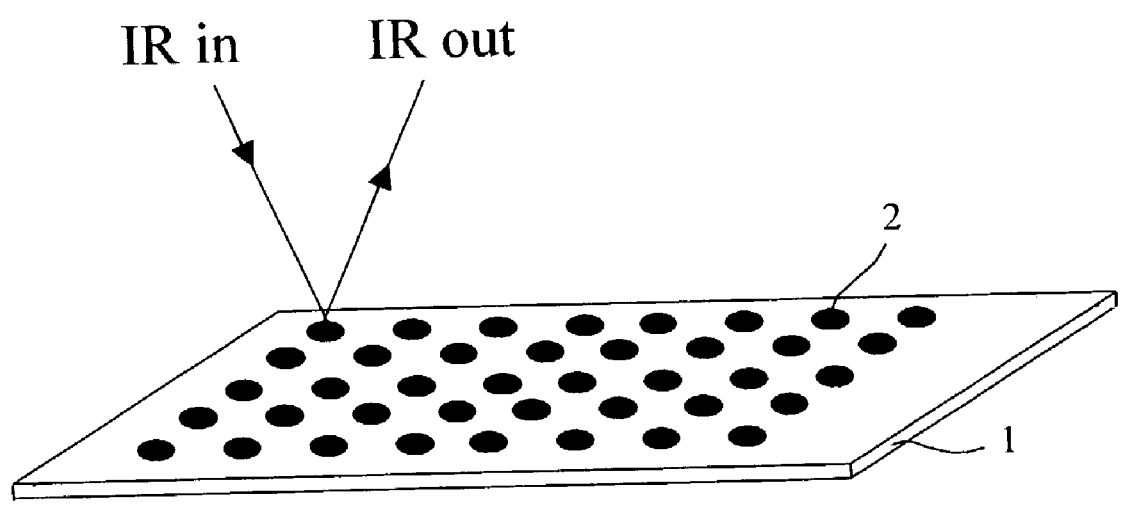
FIG. 1 is illustrated the biosensor substrate with immobilized biomolecules used in the invented infrared reflection absorption spectroscopy

The material for making a biosensor must allow for reflecting infrared lights, such as gold, silver, copper, aluminum, germanium and stainless steel sheet. A signal for the protein is obtained from determining infrared light absorption wavelength of the light bounced from the immobilized, reflecting substrate, such as the antigen or the antibody protein affixed to the sensor due to the special chemical bonding between a protein and a metal surface. According to FIG. 1, using the immobilized molecule on the surface of the substrate 1 (such as silver or gold) as the probe 2, which is selected from different kinds of molecules (such as antigen) as the probe 2 on the surface of the substrate 1, in order to allow for multiple assays. After hybridizing the molecules immobilized on biosensor with the analyte of interest (such as antibody), then placing the biosensor on the IR spectroscopy for detecting the infrared reflection absorption spectrum of samples. The detected IR spectrum can be used for characteristics and quantity of the samples.

Furthermore, the immobilizing method in the present invention is designed for infrared spectroscopy technology. For that reason, using special bonding characteristics between metal substrate and protein, one can develop a blocking agent created from low IR absorbing molecule to increase the possibility of antigen and antibody to be selected.

The present invention is about infrared reflection absorption spectroscopy. The present description and referring figures allow one to better understand the invention's novelty and utility. However, the scope of the present invention is not limited to what is being claimed. Individuals, who are knowledgeable in this area of art, without deviating from the scope and spirit of this invention, may perform appropriate embellishments and adjustments.

EXAMPLES

Figure 2:
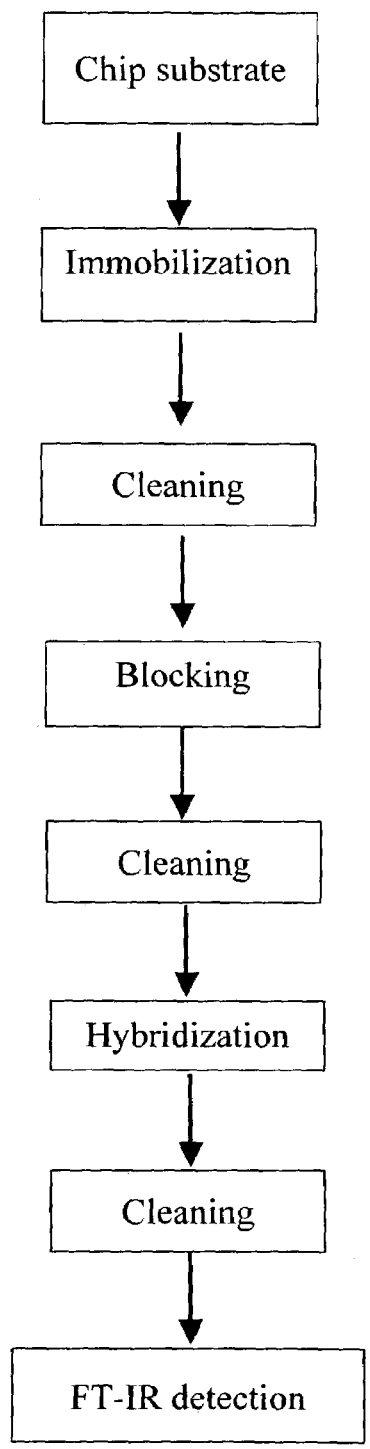
FIG. 2 is a flow chart of the infrared reflection absorption spectroscopy based immunoassay process.

A. Implementation Process: Biosensor Making and Measuring Procedures in this Invention are Delineated in FIG. 2.
   (i.) Cleaning Biosensor Substrate: In this invention, a sliver plate was used as biosensor substrate. Since silver tends to oxidize when it is exposed to air, after it has been appropriately grinded by aluminum oxide, placing the sliver plate with a solution of cleaning agent and (R.O.) distilled water in an ultrasonic screener to be cleaned for fifteen minutes. Next, decant the solution and wash the plate with distilled water.
   (ii.) Immobilizing Reaction: At this point, take 0.5 $\mu L$ of bovine IgG and 2.5% glutaraldehyde and mix the two ingredients together. The glutaraldehyde was used for cross-linking the antibody. Next, drop the above mixture onto the cleaned silver plate and let them react in a 4° C. environment for 16 hours in order to allow the antibody to immobilize on the sliver plate.
   (iii.) Cleaning: After the reaction, clean the plate with an adequate amount of PBS (phosphate buffer saline) solution in a shaker for 10 minutes and repeat this clean procedure once more.
   (iv.) Blocking procedure: At this point a solution of the appropriate concentration that contains PBS and the PVA (poly vinyl alcohol) is prepared; the PVA was used as a blocking agent to block nonspecific binding sites of the molecule. Immerse the plate as described in step (ii) in the solution for 1 hour, followed by repeating the clean procedure described in step (iii).

(v.) Hybridization: Place a solution of anti-bovine IgG and PBS at the adequate concentration with the sensor plate containing the immobilized antibody into the ultrasonic screener to undergo reactions for 2 hours. Then, clean the plate by repeating the clean procedure as described in step (iii).

(vi.) Detection: Place the sensor plate that had underwent reactions in step v in a Fourier Transform Infrared Spectrometer or infrared microspectrometer to determine its reflective absorption signals. In this invention, the spectra were measured on the infrared spectrometer, the Bruker Vector 22 with deuterated triglycine sulfate spectrometer, with 24 scans at the angle of 4 $cm^{-1}$, using cosine as the corrective function.

B. Result of Detection

Figure 3:
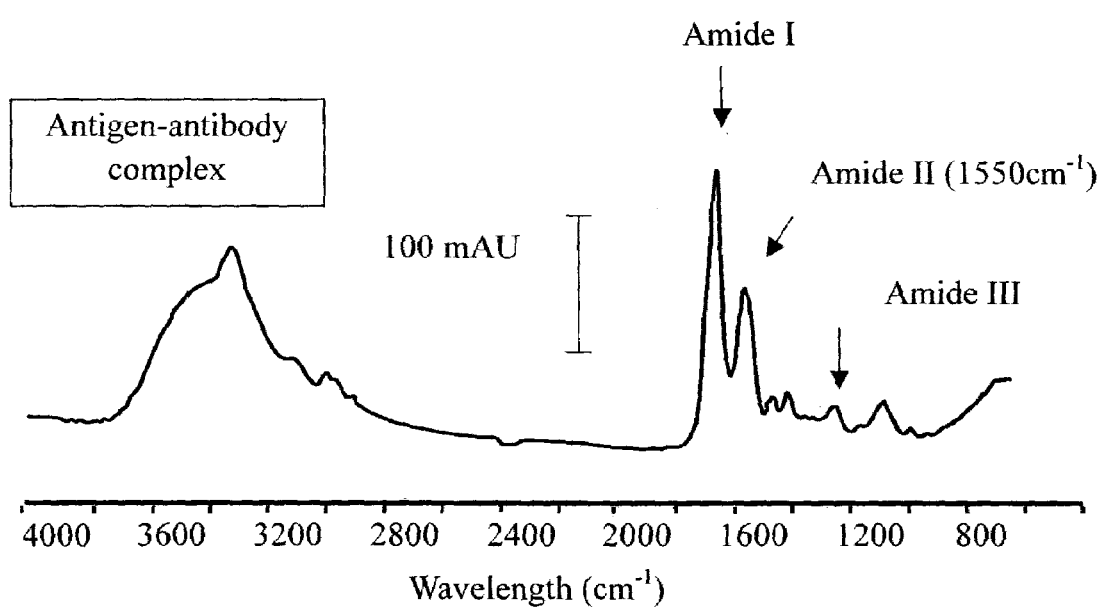
FIG. 3 is an IR spectrum of antibody-antigen complex determined from the present invention.

According to above mentioned implementation procedures, the result obtained from the Fourier Transform Infrared Spectrometer (FTIR) as outlined in FIG. 3 shows an IR spectrum of various antibody-antigen complexes, revealing that amide II has the standard absorption peak. According to the value of reflection absorption peaks in those antigen-antibody complexes, one can determine whether the analyte of interest has reacted with the molecule immobilized to the biosensor plate. Furthermore, further implementation of this experiment can calculate the amount of analyte of interest according to intensity of the amide II absorption.

The present invention uses reflective absorption to combine Fourier Transform Infrared Spectrometer to measure antigen-antibody complexes. The positive attributes in this invention are as follows: (1) Any molecule with special infrared light absorption peak can provide plenty of information on its structure. (2) There is no need to label the samples with fluorescent or emission matters for detection. (3) Quick detection and provide information on the characteristics and quantity of the analyte of interest. (4) Detecting technique does not damage the analyte of interest, allowing other methods of measurement to be made at the same time. (5) Detecting procedure allows metal plates can be used again, hence is good for the environment.

Above shows there are many positive attributes in this invention, revealing it to be an infrared light immunoassay that is efficient and economical.

What is claimed is:

1. A method for detecting an analyte of interest in a sample by using infrared reflection absorption spectroscopy which comprises:

providing an infrared reflective substrate;

immobilizing a known molecule on said substrate;

blocking non-specific bonding sites of said known molecule by contacting a blocking agent which is dissolved in a buffer with said known molecule, wherein said blocking agent is glucose, glycerol, polyallylamine, or polyvinyl alcohol;

reacting an analyte of interest with said known molecule which is immobilized on said substrate;

forming a specific binding complex of said known molecule and the analyte of interest by interaction of binding affinity of said known molecule and said analyte; and detecting infrared reflection absorption signals that reflect directly from said complex by using infrared spectroscopy in order to detect said analyte of interest.

2. The method according to claim 1, wherein said substrate is a metal or a substrate covered with a metallic layer.

3. The method according to claim 2, wherein said metal is gold, silver, copper, aluminum, germanium or stainless steel.

4. The method according to claim 3, wherein said metal is gold or silver.

5. The method according to claim 1, wherein said blocking procedure includes dissolving a blocking agent with a liquid buffer and reacting the known molecule immobilized on the substrate with said blocking agent to block the non-specific binding sites of the known molecule.

6. The method according to claim 1, wherein said blocking agent is polyvinyl alcohol or polyallylamine.

7. The method according to claim 1, wherein said molecule is a protein, antibody, antigen or receptor.

8. The method according to claim 1, wherein said molecule is an antigen or antibody.

9. The method according to claim 1, wherein the absorption wavelength of said molecule is at 1550 $cm^{-1}$.

* * * * *